(12) United States Patent
Kadir

(10) Patent No.: US 9,147,242 B2
(45) Date of Patent: Sep. 29, 2015

(54) PROCESSING SYSTEM FOR MEDICAL SCAN IMAGES

(75) Inventor: Timor Kadir, Oxford (GB)

(73) Assignee: Mirada Medical Limited, Oxford (GB)

( * ) Notice: Subject to any disclaimer, the term of this patent is extended or adjusted under 35 U.S.C. 154(b) by 177 days.

(21) Appl. No.: 13/701,876

(22) PCT Filed: Jun. 3, 2011

(86) PCT No.: PCT/EP2011/059208
§ 371 (c)(1),
(2), (4) Date: Feb. 28, 2013

(87) PCT Pub. No.: WO2011/151448
PCT Pub. Date: Dec. 8, 2011

(65) Prior Publication Data
US 2013/0156280 A1    Jun. 20, 2013

(30) Foreign Application Priority Data

Jun. 4, 2010   (GB) .................................. 1009363.1

(51) Int. Cl.
*G06K 9/00*    (2006.01)
*G06T 7/00*    (2006.01)
*A61B 6/03*    (2006.01)

(52) U.S. Cl.
CPC ............ *G06T 7/0012* (2013.01); *A61B 6/037* (2013.01); *G06T 2207/10081* (2013.01); *G06T 2207/10088* (2013.01); *G06T 2207/10104* (2013.01); *G06T 2207/10108* (2013.01); *G06T 2207/20104* (2013.01); *G06T 2207/20221* (2013.01)

(58) Field of Classification Search
CPC .................. G06T 7/0012; G06T 2207/20221; G06T 2207/10081; G06T 2207/20104; G06T 2207/10108; G06T 2207/10088; G06T 2207/10104
USPC ........... 382/100, 128–132, 159; 600/407, 408
See application file for complete search history.

(56) References Cited

U.S. PATENT DOCUMENTS

| | | | |
|---|---|---|---|
| 6,466,687 B1 * | 10/2002 | Uppaluri et al. ............... | 382/128 |
| 8,280,134 B2 * | 10/2012 | Hoyt .............................. | 382/128 |
| 2003/0103665 A1 * | 6/2003 | Uppaluri et al. ............. | 382/131 |
| 2006/0030768 A1 * | 2/2006 | Ramamurthy et al. ....... | 600/407 |
| 2007/0036402 A1 * | 2/2007 | Cahill et al. .................. | 382/128 |
| 2007/0127793 A1 * | 6/2007 | Beckett et al. ............... | 382/128 |

* cited by examiner

Primary Examiner — Shefali Goradia
(74) Attorney, Agent, or Firm — Frank M. Scutch, III

(57) ABSTRACT

A method, medical imaging workstation (300) and a hybrid medical imaging scanner (400) are provided for the analysis of images obtained during medical scans. The extent of a first region of interest (ROI-1) in a first scan image (120) is defined. A second region (ROI-2), in a second scan image (130), is identified. The second region (ROI-2) in the second scan image (130) corresponds to the first region of interest (ROI-1) in the first scan image. Each of the spatial locations of the second region (ROI-2) is classified, in order to identify the spatial locations of the second region (ROI-2) that comprise at least one tissue type. The invention may improve the recognition of lesions in medical scan images, and may reduce the incidence of false positives.

20 Claims, 7 Drawing Sheets

PROCESSING SYSTEM FOR MEDICAL SCAN IMAGES

TECHNICAL FIELD

The present invention concerns the analysis of images obtained during medical scans.

BACKGROUND ART

A variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an 'imaging modality'.

In medical imaging, typically, digital 3-dimensional images are produced. Medical imaging workstations are commonly used to allow the viewing and manipulation of these images. Medical images are read, analysed and reviewed by specialists, for example radiologists.

Typically, a scan provides a 'dataset'. The dataset comprises digital information about the value of a variable at each of many points. The points are different spatial locations that are spread throughout 3 physical dimensions, i.e. each point is at a particular location on a three dimensional grid. The variable may typically be an intensity measurement. The intensity may be, for example, an indication of the X-Ray attenuation of the tissue at each particular point.

In such a three dimensional dataset, the element of the scan image located at a particular spatial location may be referred to as a 'voxel'. A voxel is therefore analogous to a 'pixel' of a conventional 2-Dimensional image.

Although the dataset of the medical scan is 3-Dimensional, it is typically displayed as a two dimensional image to a user on a medical imaging workstation. The 3-D scan may be divided up into tens or hundreds of parallel, 2-D images. The user of a workstation can then flick through the images in sequence, for example, thereby allowing a view of successive cross sections of the tissue that was scanned.

Typical workstations allow the 2-D slices to be viewed individually or sequentially in successive steps along a selected one of three perpendicular directions. For a human subject lying down, the axes of the three perpendicular directions may, for example, be along the 'long axis' of the body, 'across' the body from one side to the other, and through the body from top to bottom. These axes are conventionally referred to as: 'axial' (for cross-sections that lie along the long axis of the body), coronal (for cross-sections that lie along an axis running from the front to back) and sagittal (cross-sections that lie along an axis that runs from side to side.)

Henceforth, the term 'scan image' should be construed as meaning a three dimensional dataset that results from performing a medical scan. However, when the scan image is displayed, only a two dimensional slice of the dataset may be on view at any one time. Medical images usually have as their subject humans. However, images may also be obtained of non-human animals, particularly as part of medical research projects.

Medical images may include information about a wide variety of anatomical features and structures. For example, an image may show various types of healthy tissue, such as bone and organs within the body. An image may also show abnormal tissues. The term 'lesion' is often used to describe various types of abnormal tissue. One common example of a lesion is a tumour. However, an image may also show other types of lesions, such as cysts or swollen glands. The word 'lesion' should henceforth be construed to include both tumours and other types of abnormal tissues.

The purpose of obtaining a medical image is often to detect abnormal tissue. So, a typical example of an application of medical imaging is in the identification and 'staging' of cancerous tumours. Images may also be required for assessing the efficacy of any administered treatment. Images from scans may however not lead unambiguously to an identification of whether or not a given part of the scan shows abnormal tissue. The identification of the pathology of tissue observed in a scan is still not possible with 100% certainty. As a consequence, for example, patients may subsequently need to be subjected to biopsies, in order to obtain a sample of tissues whose nature is not clear on a scan.

'Multiple modalities' may be used to provide medical images. This approach involves obtaining images of the same region of tissue by more than one modality. For example, the same region of tissue may be imaged using both a PET scan and a CT scan. Another important example of a multiple mode scan is a SPECT/CT scan. Both PET/CT and SPECT/CT scans combine the predominantly anatomical and structural information obtained from a CT scan with a scan which measures the biological function.

Scanners that can carry out multiple mode scans are referred to as 'hybrid scanners'. Typically, a hybrid scanner allows the subject to be scanned by both modalities in the same sitting.

A multimodal scan such as a PET/CT or SPECT/CT scan may provide the following advantages:

1) It provides the reader with both anatomical and structural information, as well as functional information.
2) The CT scan can be used to correct for the attenuation to which the SPECT or PET signal is subjected, as it travels through the body.
3) It allows the reader to localise areas of PET or SPECT signal to particular regions of the body.
4) The patient benefits from fewer examinations.
5) A given scanning machine will provide more information for any given number of patients who are scanned, than a single mode scanner, thereby delivering enhanced 'utilisation' for a hospital.

The precise biological signal measured by a PET or SPECT scan is dependent on the radiotracer used. For PET, the most widespread radiotracer is fluorodeoxyglucose (FDG), which is a sugar. FDG acts as a surrogate for glucose, thereby facilitating the measurement of metabolic activity within a region of tissue.

Malignant tumours are highly metabolically active. They therefore tend to appear as bright areas in a PET image. Such active tissues are often referred to as being 'FDG avid'.

A problem may arise due to the fact that there are many normal physiological processes that are also FDG avid. For example, the brain also consumes large amounts of energy. So the brain appears as a bright region on a PET image. The same applies to the heart, the bladder and parts of the kidneys.

Normally, such well localised anatomical regions can be identified by experienced personnel. This identification usually just requires examination of the PET image alone, and rarely requires examination of the corresponding CT image of any multimodal scan, to allow these regions to be categorically ruled out in any search for abnormal tissue. However, some lesions that are near the edges of FDG avid organs may be less clearly differentiated. In these cases, the normal way to decide the likely cause of a bright region in the PET image is by looking at the CT scan.

Other, more subtle sources of apparently FDG avid regions may be seen in images. Examples include:
(i) The larynx, which may exhibit some FDG activity if the subject spoke after injection of the radiotracer.
(ii) Artificial implants. In a PET/CT multimodal scan, the CT can be used to correct for the photon attenuation observed when the photons travel through different parts of the body. This correction process relies on a correct estimation of the attenuation that a photon undergoes. However, the presence of implants and mis-alignment of the two scans may cause errors in the estimation. The errors lead to 'artefacts' in the PET post attenuation correction.
(iii) Inflammation processes.
(iv) Metabolically active brown-fat.

These sources (i)-(iv) are more problematic than areas such as the brain, and may lead to 'false positive' diagnoses. A 'false positive' is a case where a normal area of tissue is mistakenly classified as abnormal.

In summary, a key problem in the interpretation of medical image scans is the determination of the underlying cause of apparent activity. This problem arises particularly when considering radiotracer activity in a PET or SPECT image.

Three more detailed prior art systems are listed under points 1-3 below. The 'Computer Aided Detection/Diagnosis systems' and 'Basic histogram' approach are essentially techniques for interpreting information obtained in scans. The 'MR spectroscopy' approach is a different type of scan, which provides different data to those described above.

1. Computer Aided Detection/Diagnosis Systems

Many computerised approaches have been proposed to aid the clinician in detecting and diagnosing disease. So-called 'Computer Aided Detection and Diagnosis' systems aim to do this by indicating to the user locations in the image that are likely to correspond to disease. However, such systems are designed to indicate the presence or absence of disease. They operate by examining patterns in the image, and categorising them as 'disease' or 'non-disease'. Such systems have been proposed mostly for single image, single modality applications like X-ray mammography, lung CT and colon CT. Furthermore, such systems do not integrate well into the clinical work-flow, because they tend only to show limited information about the images.

2. Basic Histogram

Medical image workstations may include functionality that enables them to display a histogram of the distribution of intensities within a user defined region of interest in a scan. Such histograms are typically 'binned' according to some uniform bin width, for example every 100 units of intensity. Alternatively, they may be specified to have a certain number of bins. Information may be provided to the user on e.g. the mean of the values in a region of interest, or the maximum.

3. Spectroscopy

MR spectroscopy is a particular type of MR scan, in which the chemical composition of regions of tissue in a patient can be identified in vivo. The method relies on the different nuclear magnetic resonance signal of different chemical compounds. The result is often displayed to the user as a graphical plot, which shows the proportion of different compounds. MR spectroscopy leads directly to an identification of the chemical composition of a region of tissue.

DISCLOSURE OF INVENTION

In accordance with a first aspect, the invention provides a method of analysing a medical scan image in accordance with claim 1. In accordance with a second aspect, the invention provides a workstation for analysing a medical scan image in accordance with claim 15. In accordance with a third aspect, the invention provides a hybrid scanner in accordance with claim 19. In accordance with a fourth aspect, the present invention provides a computer program product in accordance with claim 20.

The invention may provide a simple, fast, accurate and reproducible method for analysing a medical scan image. The invention may offer the advantage of reducing the number of 'false positives'. A false positive is a region of a medical scan image where abnormal tissue is believed to exist, but where in fact the tissue is normal.

DETAILED DESCRIPTION

A method of analysing a medical scan image in accordance with the invention may comprise the following steps:
(i) Defining the extent of a first region of interest in a first scan image. The first scan image may be one that shows biological activity within tissue. The first region of interest 'ROI-1' may, for example, be defined on the basis of the intensity of the first scan image, within a particular boundary. The boundary may be defined by a user. In a typical application, the first scan may be a PET or SPECT image, and the first region of interest 'ROI-1' may be one in which some of the tissue is FDG avid.
(ii) Identifying a second region 'ROI-2' in a second scan image. The second region in the second scan image corresponds to the first region of interest in the first scan image. The second scan image may be one that shows structural information about at least some of the same portion of tissue as the first image. In a typical application, the second scan image may be a CT scan, which shows the same portion of a body as the first scan image.
(iii) Classifying each of the spatial locations of the second region. This step provides a classification of spatial locations of the second region into at least one category of tissue type.

There may however be several categories, for example N categories. Each of the N categories is indicative of a particular tissue type.

The method provides information about the proportion of the spatial locations in the second region that correspond to each of at least one category of tissue type. These proportions may then be used in a determination of a cause of biological activity in the first region of interest.

The first scan image may show biological activity within tissue. The second scan image may show structural or anatomical information about a region of tissue that at least partially overlaps the region of tissue shown in the first scan image.

Figure 1:
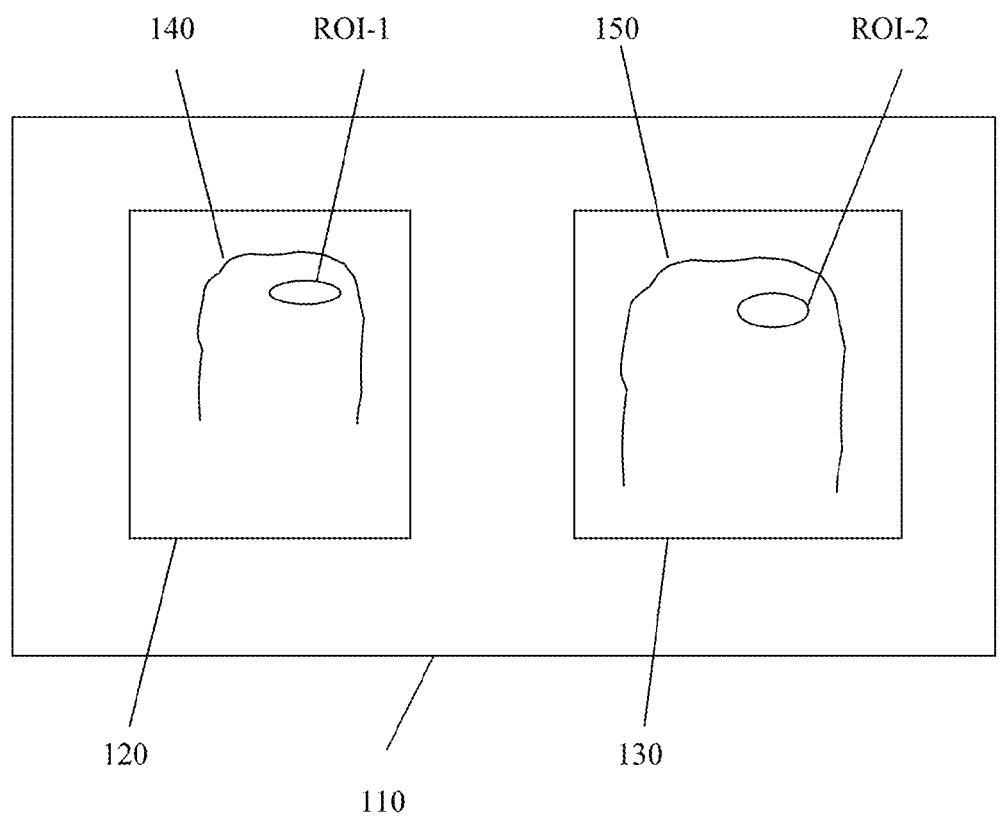
FIG. 1 shows a workstation screen with two images that may be provided in accordance with an embodiment of the invention.

FIG. 1 shows an example of a pair of medical scan images that may be displayed by a medical imaging workstation in accordance with the method of the invention.

Reference 110 shows a screen of a medical imaging workstation. The result of a first scan is shown as first scan image 120. Adjacent to first scan image 120 is the result of a second scan, which is second scan image 130. A portion of tissue generally labelled 140 is shown on first scan image 140. At a slightly different scale, the same portion of tissue is shown and labelled 150 on second scan image 130.

First region of interest ROI-1 is displayed in two dimensions on first scan image 120. The second region ROI-2 is displayed on second scan image 130.

Defining the Extent of the Region of Interest

The step of defining the extent of a first region of interest in the first scan image may be accomplished in one of several ways. Three of these are as follows:

(i) Using a 'boundary box'. The boundary box is a 3-Dimensional shape, for example a cuboid or an ellipsoid. A user may define the boundary box, based on what can be seen on the first scan. A cursor on a screen of a medical imaging workstation may be used to define the boundary box, under the control of a mouse or tracking ball. The boundary box is typically placed so as to encompass all of an object that is to be analysed. A threshold can then be set. The 'first region of interest' then comprises all the spatial locations within the boundary box at which the measured value exceeds the threshold.

(ii) A variant of approach (i) is to define a boundary box, and then find the maximum value of any spatial location within the boundary box. A percentage of the maximum value, for example 40% of the maximum intensity, is then selected as a threshold. The 'first region of interest' then comprises all the spatial locations within the boundary box at which the measured value exceeds the threshold.

(iii) The user may click on a point on the image that is of interest, for example by placing a 'cross-hair' at the point under control of a mouse or tracking ball. The workstation then works outwards from the selected point, and identifies each contiguous spatial location at which the measured value exceeds a threshold value. These spatial locations make up the first region of interest.

Figure 2:
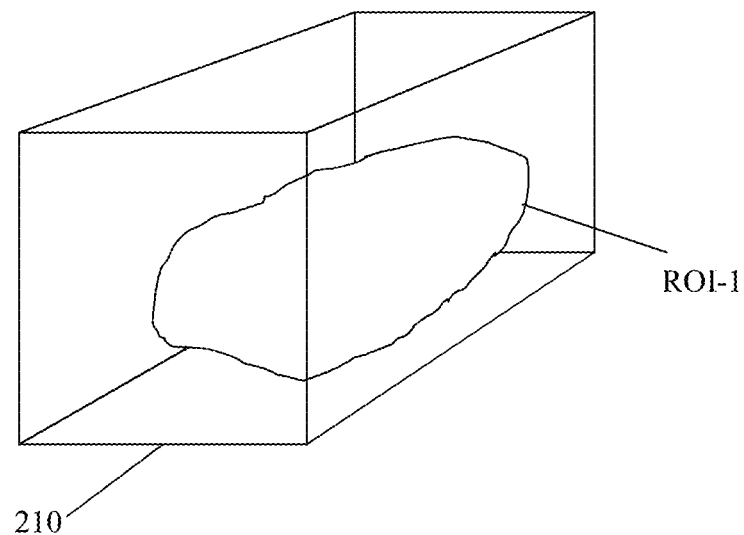
FIG. 2 shows a first region of interest that may be defined in accordance with an embodiment of the invention.

FIG. 2 shows an example of a boundary box 210 that may be used in approaches (i) or (ii) above. Within boundary box 210 is an area of tissue that the operator of a medical imaging workstation suspects may be a lesion.

In accordance with the approach outlined under (i) above, the medical imaging workstation or the hybrid scanner identifies all the spatial locations within boundary box 210 where a threshold value, for example of intensity, is exceeded. These locations form the first Region of Interest ROI-1.

The workstation would then proceed to find the spatial locations on a second scan image that correspond to ROI-1. These locations are the second region ROI-2. The second scan image 130 and ROI-2 are shown on FIG. 1.

Classifying the Spatial Locations

The step of classifying each of the spatial locations of the second region ROI-2 may comprise comparing the intensity of each voxel of the second region to at least one pre-defined range of intensity values. The pre-defined range corresponds to a particular tissue type of interest. So each spatial location, represented by a voxel, has an intensity that falls either within the predefined range, or outside it. This approach can simply total up the number of voxels of one tissue type, and the number of voxels that are not of that tissue type. If the user were simply interested in the proportion of voxels in ROI-2 that are brown fat cells, for example, then this approach could lead to that proportion, or to an absolute number of voxels.

The invention may classify each voxel into one of several (N) ranges of intensity values. Each range would correspond to a different category of tissue type.

The classification of spatial locations of the second region ROI-2 may then be used in a determination of a cause of biological activity in the first region of interest ROI-1. This determination may be most reliable when several ranges are used in the classification of voxels of ROI-2, because extra information about tissue types within ROI-2 is then available.

The step of classifying each of the spatial locations of the second region may include comparing the X-Ray attenuation of the tissue represented by each voxel with at least one range of X-Ray attenuation values. X-Ray attenuation is a measure of tissue density, so can be used to differentiate tissue types. Each of the ranges of X-Ray attenuation values, in this example, corresponds to a category of tissue type.

The method may further comprise providing an indication, if the proportion of the spatial locations in the second region that is in at least one category of tissue type exceeds a threshold. This would warn the user, for example, that tissue that is known to lead to false positives is prevalent in the first region of interest ROI-1.

The method of the invention may be implemented in either a medical imaging workstation or a hybrid scanner.

Figure 3:
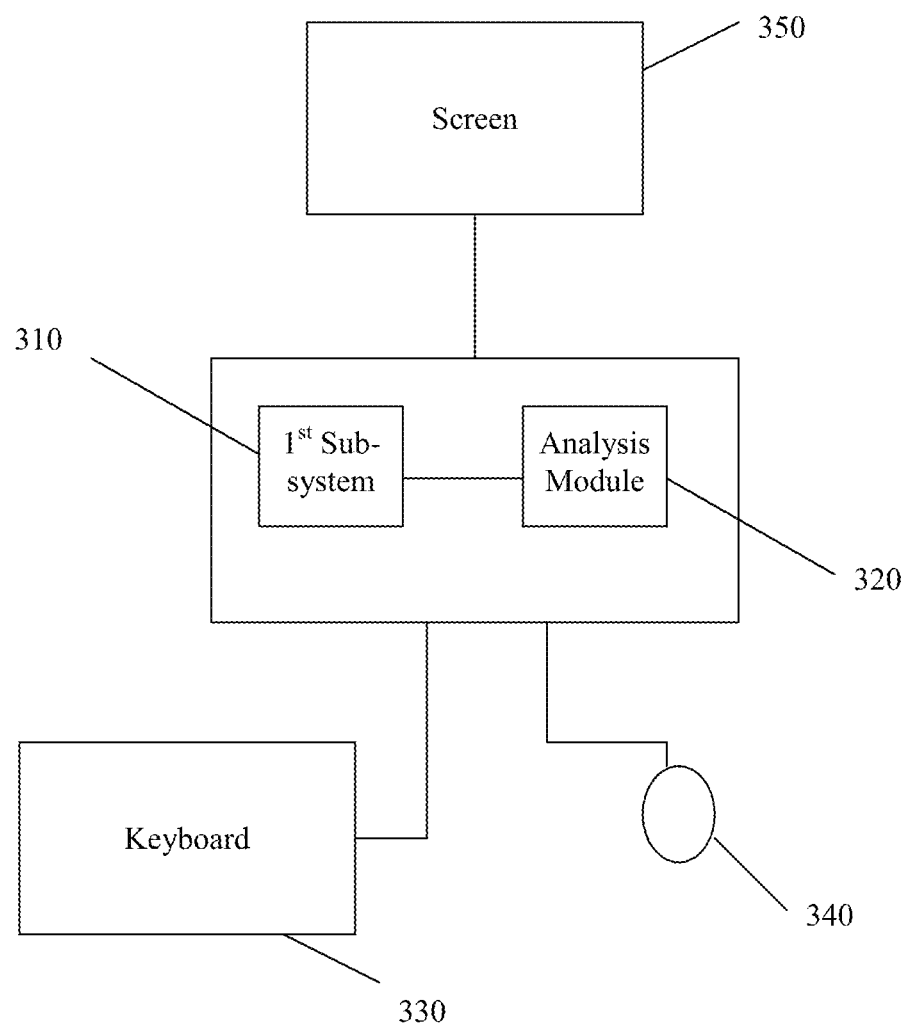
FIG. 3 shows a workstation in accordance with an embodiment of the invention.

FIG. 3 shows a workstation 300 for analysing a medical scan image in accordance with the invention. First subsystem 310 of workstation 300:

(i) defines the extent of a first region of interest ROI-1 in a first scan image; and (ii) identifies a second region ROI-2 in a second scan image, the second region in the second scan image corresponding to the first region of interest in the first scan image.

Analysis module 320 classifies each of the spatial locations of the second region ROI-2, to identify spatial locations of the second region that fall within at least one category of tissue type. Keyboard 330, mouse 340 and screen 350 facilitate communication with a user of the medical imaging workstation.

Figure 4:
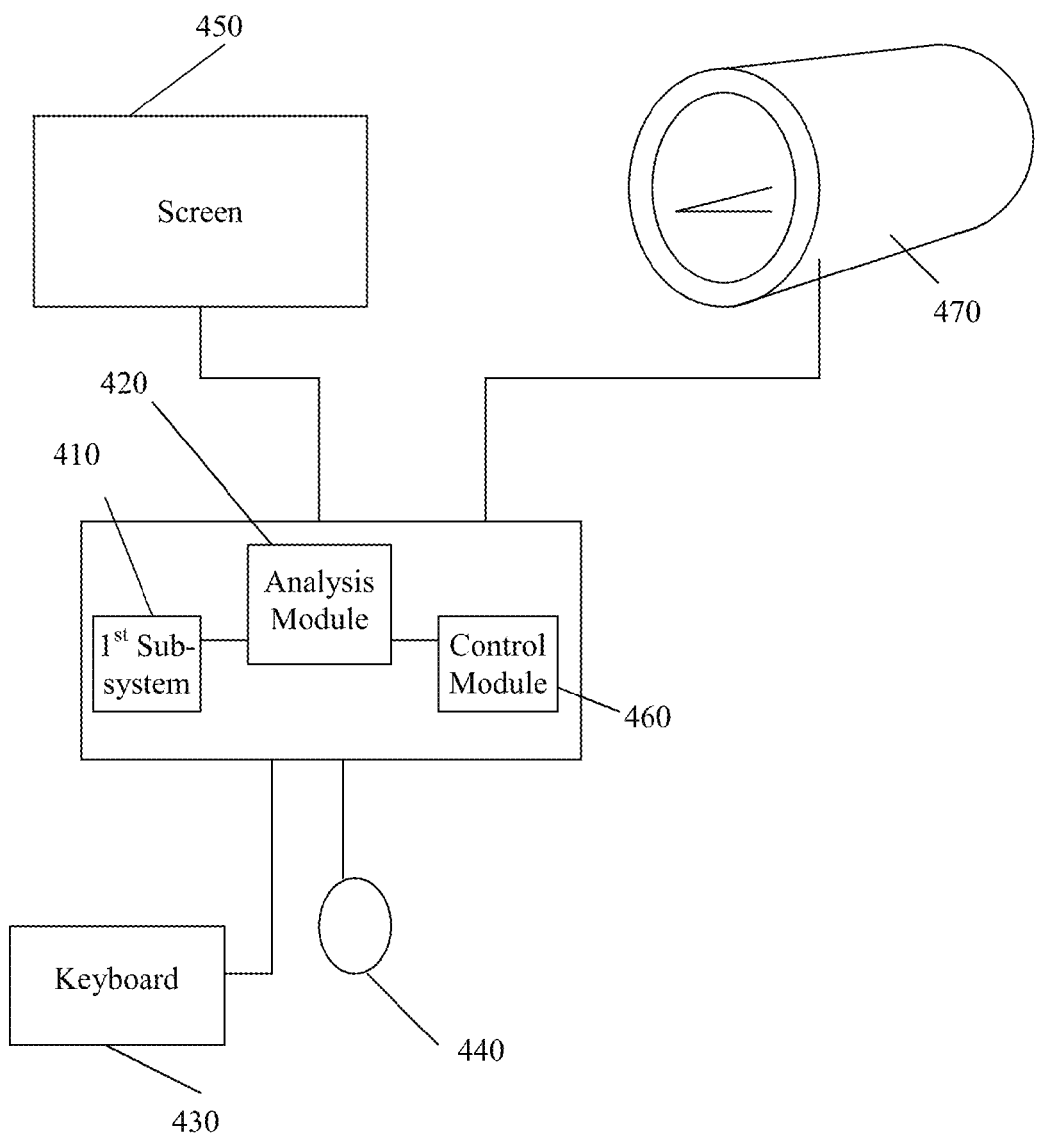
FIG. 4 shows a hybrid scanner in accordance with the present invention.

FIG. 4 shows a hybrid scanner 400 in accordance with the invention. Hybrid scanner 400 has some analogous components to those described in FIG. 3 for a medical imaging workstation 300. Hybrid scanner 400 comprises:

(i) A control module 460 that can control a scanning unit 470 to provide a first scan image and a second scan image of tissue, the first and second scan images being produced using different scanning modes.

(ii) A first subsystem 410 that defines the extent of a first region of interest ROI-1 in the first scan image. First subsystem 410 also identifies a second region ROI-2 in the second scan image, the second region in the second scan image corresponding to the first region of interest in the first scan image.

(iii) Analysis module 420, which classifies each of the spatial locations of the second region ROI-2, thereby providing a classification of the spatial locations of the second region into at least one category of tissue type.

Keyboard 430, mouse 440 and screen 450 facilitate communication with a user of the medical imaging workstation.

A computer program product in accordance with the invention has executable code for a method of analysing a medical scan image, the method comprising:

defining the extent of a first region of interest (ROI-1) in a first scan image (120);

identifying a second region (ROI-2) in a second scan image (130), the second region in the second scan image corresponding to the first region of interest in the first scan image;

classifying each of the spatial locations of the second region (ROI-2), to identify the spatial locations of the second region that comprise at least one tissue type.

Considering a method in accordance with the invention in greater detail, the method may comprise the following steps 1-4. In the exemplary method steps 1-4 provided below, the first scan image is a PET scan, and the second scan image is a CT scan. However, other image modalities may be employed. In addition, the PET scan image and the CT scan image may have been obtained in a hybrid scanner, i.e. at the same time, for the same portion of tissue. However, the scan images may have been obtained in different scanners or at different times, i.e. for portions of tissue that may only partially map onto each other. An additional fifth step is also shown, as an enhancement that may help users.

Figure 5:
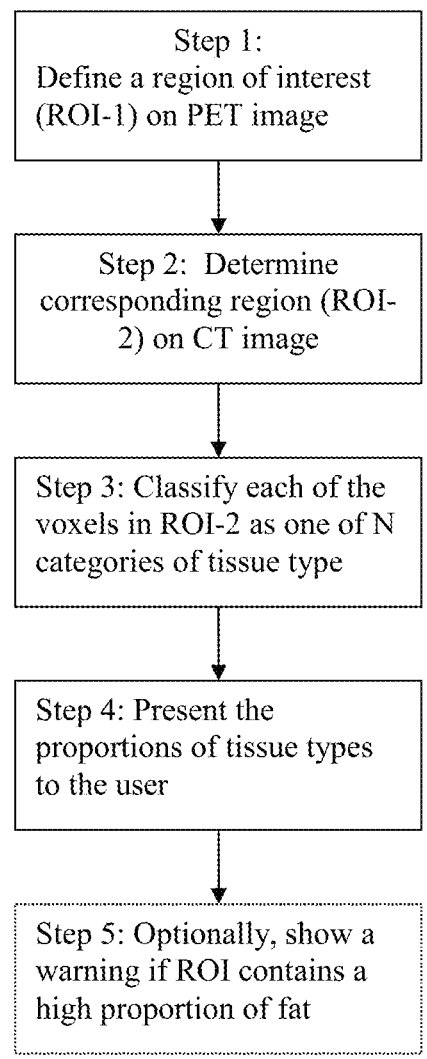
FIG. 5 shows a flowchart of a method in accordance with an embodiment of the invention

FIG. 5 illustrates steps 1-5 as a flow chart. The labels on FIG. 5 correspond to each of steps 1-5 as outlined below:

Step 1

A Region of Interest (ROI-1) is defined on the PET image. This region of interest is typically an FDG avid region.

An operator, such as a radiologist, may make this selection. The image used in this selection process may be a 2-Dimensional image viewed on a screen. That image is one of a large number of slices that together make up the 3-Dimensional PET scan image. In effect, the 2-dimensional image is provided to simplify the task of recognising where there may be FDG avid tissue. However, the PET scan holds data in 3-Dimensional space for all the spatial locations that were scanned.

Step 2

Determine the second region ROI-2 on the CT scan image that corresponds to the Region of Interest ROI-1. ROI-2 comprises a set of spatial locations in the CT scan image that correspond to the same spatial locations as ROI-1.

Step 3

Classify each of the spatial locations in ROI-2 as one of N categories of tissue type. Here the variable N is set in dependence on how many different tissues types are to be identified within the ROI-1. Each spatial location may simply be represented by a voxel of the region ROI-2. The classification may be done, for example, on the basis of the intensity of the second scan image at each spatial location in ROI-2.

Step 4

After step 3, sufficient data is available about the classification of the spatial locations of ROI-2 to present information to the user. The information may concern either the proportion of the spatial locations classified into each of the N tissue types in ROI-1, or the proportion of the spatial locations classified into a subset of the N tissue types. The subset may involve only the tissue types in which the user is most interested. These may be, for example, the tissue types that are most likely to indicate that ROI-1 is a false positive. In some cases, only one classification of tissue type may be of interest.

Step 5

Provide a warning to indicate whether ROI-2 contains a significant proportion of voxels which correspond to a particular tissue type. This warning is particularly useful in situations when 'false positives' would otherwise be produced by only looking at the PET scan. Such false positives may be caused by, for example, biological activity in fat cells. Such regions are FDG avid because of the activity of the fat cells, not because of lesions that are being sought. The warning may be set to trigger when the proportion of fat cells in the ROI-2 is greater than a given threshold. This warns the user that an FDG avid region in ROI-1 may be caused by fat cells, not by a lesion.

Steps 1-5 above provide an illustration of how the invention may be applied to PET image showing predominantly biological activity, in a case where a CT scan image is available to provide structural or anatomical information about some of the same tissue or body. However, each of these five steps may be conducted in various ways. Points 1-5 below provide greater detail and some variants of each of steps 1-5 above.

1. In step 1, various approaches may be employed to define the Region of Interest ROI-1 on the PET image. A user may define ROI-1 manually. Alternatively, a user-interactive tool, such those provided in medical image reading workstations, may be employed. Examples of such tools are ROI based 'thresholding' or 'region growing'. Typically, the user would define such a region on an FDG avid part of the image that appears to be brighter than the local background. In such a case, the user would at least suspect that the ROI-1 contains tissue that corresponds to a possible tumour.

In a further variant, the ROI-1 may also be determined by an automated algorithm that finds and delineates areas of high uptake in PET images. Such algorithms have been published and form part of the prior art.

The ROI can be determined based solely on the PET image. However, the ROI-1 can alternatively be based on the PET image and other data, such as the CT data.

2. In step 2, the region of interest ROI-1 in the PET scan is transformed into the space of the CT image. This transformation can be performed in a number of ways.

(i) In the simplest case, for a hybrid PET/CT scan taken under ideal conditions, the PET and CT images correspond exactly. Hence the PET ROI-1 can be resampled into the space of the CT. This may simply involve determining, for each PET voxel, the corresponding CT voxels.

(ii) In the case where a non-trivial transformation exists between the pair of images, the spatial transformation can be used to determine which CT voxels correspond to each PET voxel. Such a transformation may be linear and uniformly applied to the images, or may be non-linear and non-uniformly applied. The latter can correct for motion or variations in subject position between the two scans. Linear and non-linear registration algorithms can be used to fit an appropriate spatial transformation between the two images, and are particularly useful for non-hybrid data. So a typical situation in which the PET scan was not performed on the same scanner at the same time as the CT scan, and in which there is no fixed set of spatial reference points that can be applied to both scans, can be addressed by a linear or a non-linear registration algorithm.

3. In step 3, each spatial location in the second region ROI-2 is classified.

Each spatial location in the second region ROI-2 may be represented by a voxel. Each voxel is then classified into one of several relevant categories, based on the information available within the CT scan. A simple way of doing this for CT images is to use each voxel's intensity. This is possible, because the intensity of a voxel is an absolute measure of the X-ray attenuation of the tissue that the voxel represents. This attenuation is, in turn, a measure of the density of the tissue.

The X-Ray attenuation is usually measured in 'Hounsfield' units. For example, the following values are typical: Air −1000, Fat −120, Water 0, Muscle +40, Contrast Agent +130, Bone +400 or more. 'Contrast Agent' is an injected substance, for example iodine, that allows some tissues to be better differentiated in a CT scan. Contrast Agent attenuates X rays, so is bright in a CT scan image.

A range can be constructed for each of these tissue types, plus the Contrast Agent. For example, a range of +20 to +100 may be the range for 'muscle'. Each voxel can then be classified into the relevant range. For other scan modalities, the classification step may be more sophisticated, in dependence on the information that the scan provides.

The ranges used in the classification step may be under user control. The user would define the ranges, for example by entering the limit values for each range into a workstation. The ranges are thereby effectively set for the particular tissues that the user is interested in recognising. Alternatively, a workstation may be pre-loaded with limit values for some or all of the ranges to be used in the step of classifying the spatial locations of the second region ROI-2.

4. In step 4, an indication of the categories present in the ROI-2, which corresponds to the user defined region ROI-1, is presented to the user.

Statistical information may be provided in order to show the proportion of the spatial locations in each range, and hence the proportions of each tissue type. This statistical information may be in the form of:
(i) A graph showing the relative composition of tissue types;
(ii) A set of numbers indicating the fraction of each type, or the percentage;
(iii) A colour overlay or other appropriate means.

The presentation may show all the categories or only some summary of them. For example, the statistical information may relate to only the dominant one or two tissue types.

5. In step 5, optionally, the user may be provided with a warning.

In some situations, it may be advantageous to display an indication to the user if certain conditions are met. One example might be if the user has indicated that a region is a possible lesion, but the region both exhibits high FDG activity and corresponds to a fatty region. The warning would then indicate to the user that this region might be a false positive. The system may also display some confidence information relating to the measurement. For example, this might be a comparison of the proportion of fat tissue present in the ROI to some pre-defined examples.

Figure 6:
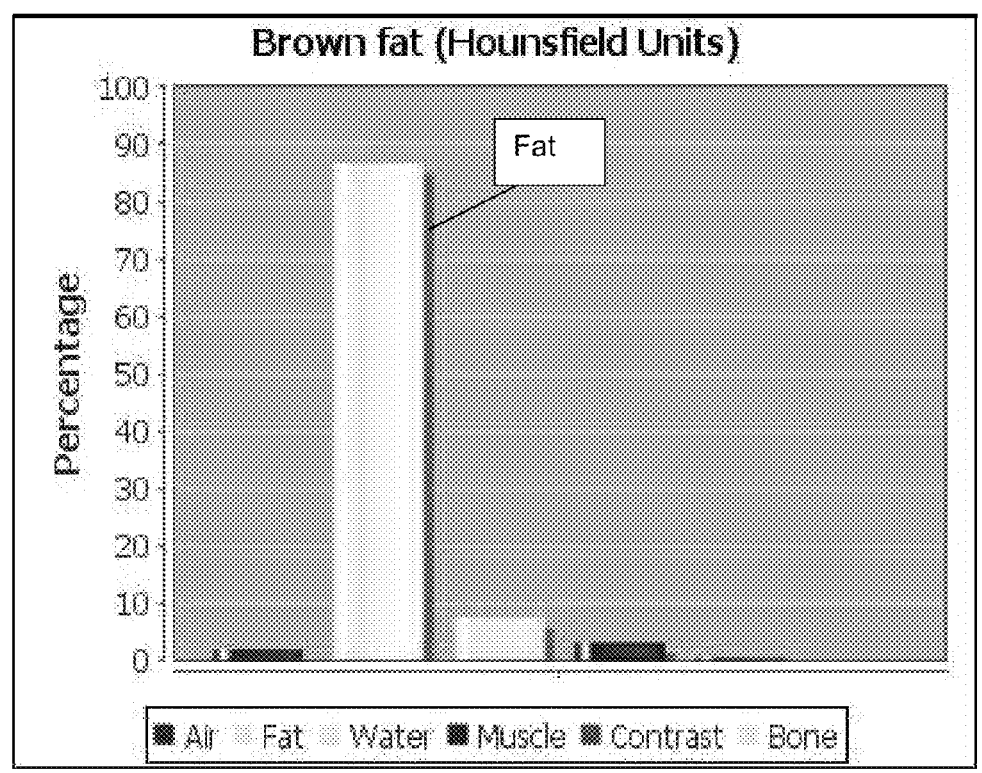
FIG. 6 shows statistics for a 'false positive' that may be displayed in accordance with an embodiment of the invention.

FIG. 6 shows a bar graph of an example of results that may be displayed to a user of a medical imaging workstation or a hybrid scanner, in accordance with the invention. The percentages in FIG. 6 show the proportions of each spatial location in a second region ROI-2 that have been classified into the categories: Air; Fat; Water; Muscle; Contrast; Bone.

FIG. 6 shows that the second region, in this example, comprises around 85% brown fat cells. This may indicate to the user a significant risk that the object in the first region of interest ROI-1 is in fact FDG active only because of the presence of brown fat cells. If this is the case, then it is not likely to be a lesion. In prior art systems, such a region might be taken as a (false) positive, i.e. it would be assumed to be a lesion.

Figure 7:
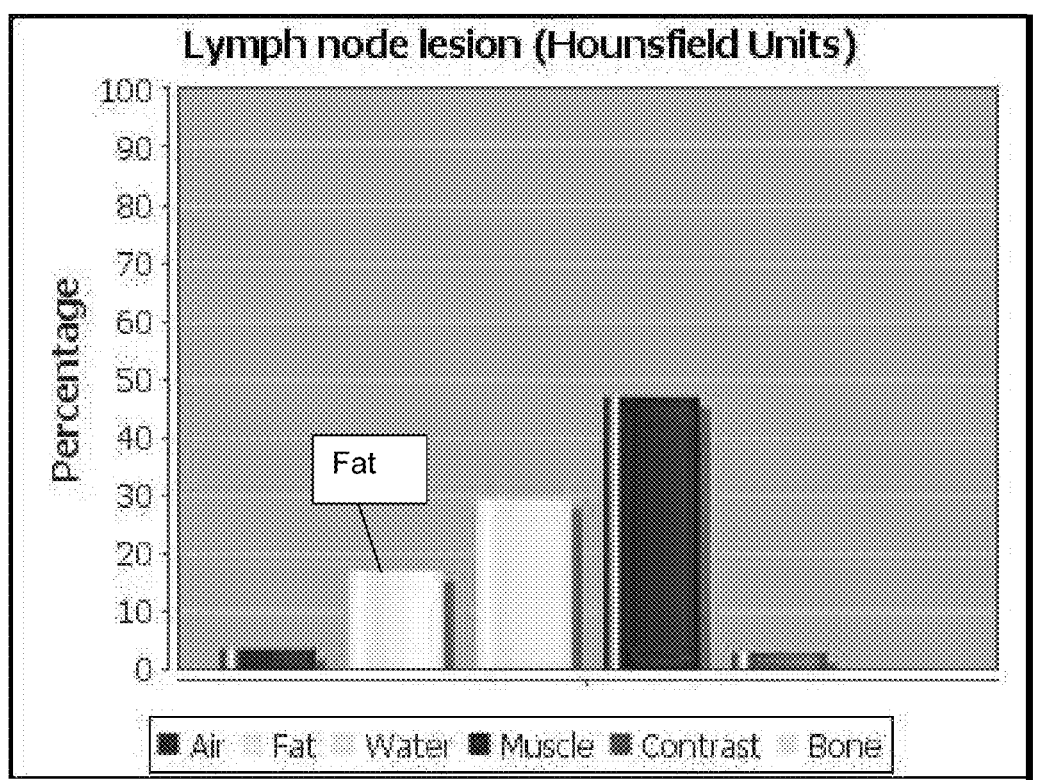
FIG. 7 shows statistics for a lesion that may be displayed in accordance with an embodiment of the invention.

FIG. 7 shows a bar graph of a second example of results that may be displayed to a user of a medical imaging workstation or a hybrid scanner, in accordance with the invention. FIG. 7 shows, for a different example of second region ROI-2, the proportions of each spatial location that have been classified into the same categories as used in FIG. 6.

The first region of interest ROI-1 in the case of FIG. 7 did in fact contain a lymph node lesion. The proportions of the spatial locations in second region ROI-2 shown in FIG. 7 are very different than those shown in FIG. 6. In FIG. 7, only around 15% of the spatial locations in ROI-2 are classified as fat. The user may conclude that there is very little likelihood that region ROI-1 was therefore FDG avid because of brown fat. Instead, the ROI-1 is likely to indicate a lesion, such as a tumour.

The embodiments of the invention described above have been illustrated by the example of a PET scan as the first scan, and a CT scan as the second scan. However, the invention may be applied to any of the following scans: X-Ray; Computed Tomography (CT); Ultrasound (US); Magnetic Resonance Imaging (MRI); Single Photon Emission Tomography (SPECT); and Positron Emission Tomography (PET).

MRI scans offer very detailed images. It is possible to apply the invention to two medical scan images that both show structure, rather than one showing biological function and the other showing structure. So, for example, the first scan may be a CT scan showing structure. The second scan may be an MRI scan, showing more anatomical detail of a first region of interest.

The invention also extends to an arrangement whereby a third region (ROI-3) is identified in a third scan image, the third region corresponding to the first region of interest ROI-1 in the first scan image. In this arrangement, each of the spatial locations of the third region (ROI-3) is also classified. The result is a classification of spatial locations in the third region, into at least one category of tissue type. In this arrangement, the third scan image may show structural information about the same tissue as the first and second images. Statistical information can then be provided about the classification(s) of the spatial locations in both the second and third regions. The statistical information may be used in a determination of a cause of biological activity in the first region of interest.

In one example in accordance with the preceding paragraph, with more than two datasets per time point, there may be a PET scan, a CT scan and an MRI scan. In this case, the system may use the information in both the CT and the MRI scans to perform voxel classifications. These may be performed by building a 'joint classifier', which has a model of how the CT and MRI intensities vary according to the category of tissue.

In its most general form, therefore, the invention may be applied to two or more medical scan images. Relative to the first medical scan image, the second medical scan image may have been obtained:
(i) At the same time, in the same hybrid scanner, as the first image.
(ii) At the same time, in a different scanner than was used for the first image;
(iii) At a later time, for example a month or more later than the first scan image.

The third and any other medical scan images that are used may be obtained as described in (ii) and/or (iii) above. In cases (ii) and (iii), registration algorithms are needed to align the spatial locations in the different images.

The invention as described so far may be varied in many ways. Each subheading A-E below explains one or more variations.

A. Single Image Over Time

A single image type, such as a PET scan, may be obtained more than once. A period of weeks or months may typically elapse between the capture of each scan image. The voxels in a region of interest may be classified for each image. The percentage of voxels in each category may then be tracked over time.

The statistics produced in this case then relate to multiple images acquired over time. This is a so-called 'longitudinal' analysis. Here the region of interest in the second and any subsequent scans can be denoted ROI-2, ROI-3, ROI-i etc. As each ROI-i is identified across the multiple time points, the system may display the voxel classification information in each time point separately. This may be useful for evaluating the change in the tissue to which ROI corresponds, for example due to treatment.

B) Multiple Images Over Time

This is an extension of the PET/CT example given above to the multiple time point case. Here ROI-1(i) is defined in each PET image taken at a given time point. The voxel classification in each corresponding second region ROI-2(ii), in each CT image, is shown to the user. ROI-1(i) may be defined by the user. Alternatively, ROI-1(i) may be propagated from an initial ROI that is defined on one image using a transformation between the time points. The transformation can be found using a registration algorithm applied to either modality.

C) Weight the Categorisation Step

The categorisation step may be weighted according to the PET uptake, when the voxel intensities are aggregated into the ranges. This is an extension to the PET/CT example given above. In the simple case of presenting the proportion of voxels in each CT voxel category, the system could weight the contribution of each voxel according to some measure of significance.

For example, the system could consider as more significant those voxels in the CT scan that correspond to a higher PET intensity. This would emphasise those voxels which correspond to a higher metabolic activity. The result provided to the user would be more tuned to the entity of interest, for example the FDG avid tumour itself. This approach may reduce the accuracy of the ROI delineation that is required around the object of interest.

D) Non-Absolute Modalities

For certain modalities, such as MRI scans, the intensity is not absolute. The approach outlined in the above description may then be modified. One solution to this problem is to normalise the image in some manner. Normalisation can be achieved in a number of ways that are themselves known in the prior art, for example by normalising the maximum and minimum values. Alternatively, the mean and variance can be normalised.

An alternative approach when the intensity is not absolute is to measure the intensity relative to some pre-defined reference regions. For example, reference regions can be defined on known structures or organs, and the intensities relative to these can be used to indicate the tissue category.

Yet another alternative is to classify the tissue region according to its pattern. In the field of image processing, such techniques are referred to as 'texture analysis'.

E) Variable Datasets at Run-Time

In certain circumstances, there may be any number of scans available that correspond to the region of interest under examination. In particular, this situation arises in MRI based analysis, where a multitude of MRI sequences are typically acquired. However, the exact sets of image in each specific sequence may vary according to the hospital in which the sequence was obtained, and across diseases.

Each sequence may be designed to highlight and/or suppress various different tissue types. For example, certain sequences suppress fat, whereas others may highlight fat. Due to the variability in the scanning protocols, the system cannot assume in advance the presence or absence of certain sequences. In this case, the approach taken in applying the invention may involve analysing each available sequence individually. Then the information is aggregated to produce an overall classification. In detail the modification operates according to the following steps:

Firstly, for each available MRI dataset
a) The system examines any meta-data that is present in the header of the file, to determine the specific protocol that has been used.
b) The second region of interest ROI-2 is defined, corresponding to the previously defined ROI-1.
c) The voxels within ROI-2 are classified according to a classification scheme that is specific for that dataset. The reliability or confidence of the classification may also be calculated, in order to aid the following step.

Next, the overall classification can be determined for each voxel in ROI-2, using the individual classification for each MRI dataset. The overall classification can be made more reliable by using information regarding the confidence of each individual classification. There are many methods for pattern classification available in the prior art. A simple approach is to use voting. With the voting approach, for each voxel, the category which obtains the most votes across the different datasets is selected as the dominant voxel class.

Advantageously, this approach can derive benefit from any MRI scans that are available, without building a specific model for each possible combination. In addition, there may be scan results from other modes that are also available for some or all of these time points. The method may also include classification results for spatial locations in the scans from those other modes.

The invention may be applied in a variety of situations. These include the following:

Picture archiving and communication systems (PACS);
Radiological information systems (RIS);
Hospital information systems (HIS);
Advanced visualisation workstations;
Imaging Acquisition Workstations;
Web based or cloud based medical information and image systems.

The invention claimed is:

1. A method of analysing a medical scan image, the method comprising:
defining an extent of a first region of interest in a first scan image;
identifying a second region in a second scan image, the second region in the second scan image corresponding to the first region of interest in the first scan image;
classifying each spatial location of the second region, to provide a classification of the spatial locations of the second region into at least one category of tissue type; and
providing information about a proportion of the spatial location in the second region that correspond to the at least one category of tissue type.

2. A method in accordance with claim 1, wherein:
the step of classifying further comprises identifying the spatial locations of the second region that correspond to each of N categories of tissue type.

3. A method in accordance with claim 2, further comprising:
providing information about proportions of the spatial locations in the second region that correspond to each of the N categories of tissue type.

4. A method in accordance with claim 1, further comprising:
determining a cause of biological activity in the first region of interest, by using information about the proportion of the spatial location in the second region that correspond to the at least one category of tissue type; and/or presenting information to a user about the proportion of the spatial location in the second region that corresponds to the at least one category of tissue type.

5. A method in accordance with claim 1, wherein:
the first scan image shows biological activity within tissue, and the first region of interest is defined at least on the basis of the intensity of the first scan image within a boundary;
the second scan image shows structural information about a region of tissue that at least partially overlaps the region of tissue shown in the first scan image;
the step of classifying each of the spatial locations of the second region comprises comparing the intensity of each voxel of the second region to at least one pre-defined range of intensity values, each range of intensity values being defined so as to correspond to a different category of tissue type; and
using the classification of spatial locations of the second region in a determination of a cause of biological activity in the first region of interest.

6. A method in accordance with claim 1, wherein:
classifying each spatial location of the second region comprises comparing an X-Ray attenuation of the tissue represented by each voxel with at least one range of X-Ray attenuation values, each range of X-Ray attenuation values corresponding to a category of tissue type.

7. A method in accordance with claim 1, further comprising:
providing a warning if the proportion of the spatial locations in the second region in at least one category of tissue type exceeds a threshold.

8. A method in accordance with claim 1, wherein:
the first scan image is one of either a Positron Emission Tomography (PET) scan image or a Single Photon Emission Tomography (SPECT) scan image; and
the second scan image is one of either a Computer Tomography (CT) scan image or a Magnetic Resonance Imaging (MRI) scan image.

9. A method in accordance with claim 1, wherein:
the first scan image is one of either a Computer Tomography (CT) scan image or a Magnetic Resonance Imaging (MRI) scan image; and
the second scan image is also one of either a Computer Tomography (CT) scan image or a Magnetic Resonance Imaging (MRI) scan image.

10. A method in accordance with claim 1, further comprising:
identifying a third region in a third scan image, the third scan image showing information about the same tissue as the first image, and the third region in the third scan image corresponding to the first region of interest in the first scan image;
classifying each of the spatial locations of the third region, to provide a classification of spatial locations in the third region into at least one category of tissue type;
providing statistical information about the classification(s) of the spatial locations in the second and third regions; and
using the statistical information in a determination of a cause of biological activity in the first region of interest.

11. A method in accordance with claim 10, wherein:
the third scan image is obtained at least one month after the second scan image.

12. A method in accordance with claim 10, wherein:
the third scan image shows structural information.

13. A method in accordance with claim 10, further comprising:

deriving statistical information showing the change over time in the proportion of the spatial locations in the second region in each category of tissue type.

14. A method in accordance with any previous claim 1, wherein, the step of identifying a second region in a second scan image uses a registration algorithm to provide a spatial transformation, thereby identifying voxels of the second scan image that correspond to voxels in the first region of interest.

15. A workstation for analysing a scan image, the workstation comprising:
a first subsystem arranged to:
(i) define an extent of a first region of interest in a first scan image; and
(ii) identify a second region in a second scan image, the second region in the second scan image corresponding to the first region of interest in the first scan image; and
an analysis module arranged to:
(i) classify each spatial location of the second region to provide a classification of the spatial locations of the second region into at least one category of tissue type; and
(ii) provide information about a proportion of the spatial locations in the second region that correspond to the at least one category of tissue type.

16. A workstation in accordance with claim 15, further comprising:
a display subsystem, for presenting information to a user about the-proportions of the spatial locations in the second region that correspond to each category of tissue type.

17. A workstation in accordance with claim 16, further comprising:
the analysis module being adapted to use the proportions in a determination of a cause of biological activity in the first region of interest.

18. A workstation in accordance with claim 15, further comprising:
the first subsystem being arranged to define the extent of the first region of interest on the first scan image at least on the basis of the intensity of the first scan image within a boundary, wherein the first scan image shows biological activity within tissue, and the second scan image shows structural information about a portion of tissue that at least partially overlaps the portion of tissue shown in the first scan image;
the analysis module is arranged to:
(i) classify each of the spatial locations of the second region by comparing the intensity of each voxel of the second region to at least one pre-defined range of intensity values, each range of intensity values being defined so as to correspond to a different category of tissue type; and
(ii) use the classification of spatial locations of the second region in a determination of a cause of biological activity in the first region of interest.

19. A hybrid medical imaging scanner, comprising:
a control module, the control module being operable to control a scanning unit to obtain a first scan image and a second scan image of a portion of tissue, the first and second scan images being produced using different scanning modes;
a first subsystem, the first subsystem being operable to:
(i) define an extent of a first region of interest in the first scan image;
(ii) identify a second region in the second scan image, the second region in the second scan image corresponding to the first region of interest in the first scan image; and an analysis module, the analysis module being operable to:
(i) classify each spatial location of the second region, thereby providing a classification of the spatial locations of the second region into at least one category of tissue type; and
(ii) provide information about a proportion of the spatial locations in the second region that correspond to the at least one category of tissue type.

20. A non-transitory computer program product having executable program code stored therein, the executable program code operable for, when executed at a workstation, performing a method of analysing a medical scan image according to claim 1.

* * * * *